US012797084B2

(12) United States Patent
Dumpe et al.

(10) Patent No.: US 12,797,084 B2
(45) Date of Patent: Nov. 17, 2026

(54) SMART TOOL

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Samuel C. Dumpe, Sewickley, PA (US); Constantinos Nikou, Monroeville, PA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 118 days.

(21) Appl. No.: 18/966,382

(22) Filed: Dec. 3, 2024

(65) Prior Publication Data

US 2025/0195086 A1 Jun. 19, 2025

Related U.S. Application Data

(60) Provisional application No. 63/610,704, filed on Dec. 15, 2023.

(51) Int. Cl.
*A61B 17/16* (2006.01)
*A61B 34/20* (2016.01)
(Continued)

(52) U.S. Cl.
CPC ...... *A61B 17/1622* (2013.01); *A61B 17/1624* (2013.01); *A61B 17/1626* (2013.01);
(Continued)

(58) Field of Classification Search
CPC .......... A61B 2090/031; A61B 17/1624; A61B 17/1626; A61B 17/1628; A61B 17/1631; A61B 17/1666
See application file for complete search history.

(56) References Cited

U.S. PATENT DOCUMENTS 5,993,454 A * 11/1999 Longo .................... B23Q 5/048 606/85
6,810,656 B2 * 11/2004 Kortum ..................... F02K 1/76 310/78
(Continued)

FOREIGN PATENT DOCUMENTS

WO 2016/199152 A1 12/2016

*Primary Examiner* — Matthew J Lawson
(74) *Attorney, Agent, or Firm* — KDW Firm PLLC

(57) ABSTRACT

An inline coupling device for a tool to engage, disengage, or regulate torque from a driver on a driveshaft based on the position and orientation of an element of the tool. In some examples, the inline coupling device may include a driver coupling shaft to couple with a surgical driver; an output shaft hub to couple with the driveshaft; a coupling device to engage, disengage, or regulate torque from the driver to the driveshaft; a communications interface to communicate with a computer system to receive an instruction to engage, disengage, or regulate the torque from the driver to the driveshaft; a coupling driver coupled with the coupling device to cause engagement, disengagement, or throttling of the torque; a power source to power the communications interface and the driver; and a housing for the inline coupling device, which may be a portion of a handle for the tool.

17 Claims, 5 Drawing Sheets

(51) Int. Cl.
*A61B 90/00* (2016.01)
*A61B 17/00* (2006.01)

(52) U.S. Cl.
CPC ...... *A61B 17/1628* (2013.01); *A61B 17/1666* (2013.01); *A61B 34/20* (2016.02); *A61B 2017/00221* (2013.01); *A61B 17/1631* (2013.01); *A61B 2034/2055* (2016.02); *A61B 2090/031* (2016.02); *A61B 2090/3983* (2016.02)

(56) References Cited

U.S. PATENT DOCUMENTS

| | | | | |
|---|---|---|---|---|
| 8,894,654 | B2 * | 11/2014 | Anderson | B25B 21/002 173/176 |
| 11,266,511 | B1 * | 3/2022 | Hughes | A61B 90/03 |
| 11,432,828 | B1 * | 9/2022 | Lang | A61B 17/1622 |
| 11,576,684 | B2 * | 2/2023 | McGinley | A61B 90/98 |
| 11,589,879 | B2 * | 2/2023 | Nino | B25B 23/141 |
| 2013/0041371 | A1 * | 2/2013 | Yates | A61B 18/1445 606/45 |
| 2016/0206328 | A1 * | 7/2016 | Lo | A61B 17/1626 |
| 2016/0305497 | A1 * | 10/2016 | Victor | F16D 9/06 |
| 2018/0222023 | A1 * | 8/2018 | Nino | B25B 23/147 |
| 2019/0216520 | A1 * | 7/2019 | Babak | A61F 2/461 |
| 2020/0093555 | A1 * | 3/2020 | Flatt | A61B 34/30 |
| 2020/0222061 | A1 * | 7/2020 | Hines | A61B 17/162 |
| 2021/0068795 | A1 | 3/2021 | Nikou et al. | |
| 2022/0233225 | A1 * | 7/2022 | Pedicini | A61B 17/92 |
| 2023/0397916 | A1 * | 12/2023 | Flatt | A61B 17/1617 |
| 2025/0100115 | A1 * | 3/2025 | Sharifi-Mehr | B25F 5/001 |

* cited by examiner

SMART TOOL

CROSS-REFERENCE TO RELATED APPLICATIONS

This application claims priority under 35 U.S.C. § 119 to a provisional patent application, U.S. Provisional Patent Application Ser. No. 63/610,704 filed on Dec. 15, 2023. The contents of the aforementioned provisional patent application is incorporated herein by reference in its entirety.

FIELD OF THE DISCLOSURE

The present disclosure relates generally to orthopedic devices and methods and more particularly to an instrumentation set including an inline coupling device between a driver and a driveshaft of, e.g., a reamer or other tool to control the tool.

BACKGROUND OF THE DISCLOSURE

Orthopedic fixation devices (implants) may be used, for example, to stabilize an injury, to support a bone fracture, to fuse a joint, and/or to correct a deformity. Orthopedic fixation devices may be attached permanently or temporarily, and may be attached to the bone at various locations, including implanted within a canal or other cavity of the bone. Some orthopedic fixation devices allow the position and/or orientation of two or more bone pieces, or two or more bones, to be adjusted relative to one another. Orthopedic fixation devices are generally machined or molded from isotropic materials, such as metals including, for example, titanium, titanium alloys, stainless steel, cobalt-chromium alloys, and tantalum.

During hip replacement surgery, also referred to as a total hip arthroplasty (THA), a surgeon may use a straight reamer and/or an offset reamer to remove the damaged sections of the hip joint and replace the damaged sections of the hip joint with parts usually constructed of metal, ceramic, and very hard plastic. This artificial joint (prosthesis) may help to reduce pain and improve function. Hip replacement surgery is typically an option when hip pain interferes with a patient's daily activities and nonsurgical treatments have not helped or are no longer effective.

Another type of orthopedic fixation device is an intramedullary ("IM") nail. The primary function of the IM nail is to stabilize the fracture fragments, and thereby enable load transfer across the fracture site while maintaining anatomical alignment of the bone. Currently, there are a large number of different commercially available IM nails in the marketplace.

In use, an IM nail is arranged and configured to be inserted into the intramedullary canal of a patient's bone, such as, for example, a patient's femur. In preparing a patient's femur to receive an IM nail, the patient may be positioned in the supine or lateral position. Next, an incision may be made and an optimal entry point may be identified. Instrumentation including, for example, an outer tube or sleeve, a handle, and a reamer may be used to ream the patient's intramedullary canal to receive the IM nail.

Recent techniques employ robotic and navigation assisted surgery. The surgeon may enter a pre-operative plan to follow during surgery and optics or robotics may assist in navigation during the surgery to follow the pre-operative plan. One concern during such procedures relates to the avoidance of removing bone other than the bone identified for removal in the pre-operative plan.

It would be beneficial to provide ensure that a reamer only operates when in a correct position and orientation relative to a bone for bone removal, in accordance with a pre-operative plan, to facilitate navigation-assisted or robotic-assisted surgical procedures through implementation of additional safety measures. It would be beneficial to ensure a procedure, such as a total hip arthroplasty procedure, is completed in accordance with a pre-operative plan by implementing robotic control of a reamer assembly. Only actuating the reamer when oriented in a position and orientation facilitating bone removal in accordance with the plan may prevent a deviation from the plan that might lead to a sub-optimal result.

It is with respect to these and other considerations that the present disclosure may be useful.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In some examples, inline coupling device for a reamer arranged and configured to facilitate, e.g., a Total Hip Arthroplasty is disclosed. In some examples, the inline coupling device may a driver coupling shaft to couple with a surgical driver; an output shaft hub to couple with a reamer driveshaft; a coupling device to engage or disengage torque from the driver to the reamer driveshaft; a communications interface to communicate with a computer system to receive an instruction to engage or disengage the torque from the driver to the reamer driveshaft; a coupling driver coupled with the coupling device to cause engagement or disengagement of the torque; a power source to power the communications interface and the driver; and a housing for the inline coupling device.

In any preceding or subsequent example, inline coupling device further including a mount for an optical target array to couple optical targets with the housing.

In any preceding or subsequent example, inline coupling device further including the computer system, wherein the computer system includes memory with code, wherein the code, when executed by a processor of the computer system, causes the processor to access to a translation between the optical targets and a reamer element of the reamer, determine a location of the reamer element, determine whether to engage or disengage the torque based on the location of the reamer element, and transmit a command to the wireless communications interface to engage or disengage the torque.

In any preceding or subsequent example, wherein the coupling device includes an electrostatic clutch assembly, a friction clutch assembly with a linear actuator, a geared interface assembly, an inline brake device assembly, an electroadhesive clutch assembly, an electrorheological fluid-based clutch, or other assembly with comparable functionality.

In any preceding or subsequent example, wherein coupling device includes an electrostatic clutch assembly, the electrostatic clutch assembly including an electrostatic driving plate, wherein the coupling driver, the power source, and the wireless communications interface are coupled with a surface of the electrostatic driving plate directly or via an adapter plate.

In some of the preceding or subsequent example, wherein the electrostatic driving plate is coupled within the electrostatic clutch assembly proximate to a driven plate via one or more fasteners.

In any preceding or subsequent example, wherein the electrostatic driving plate couples with the driver coupling shaft via a shaft hub and a sleeve for the shaft hub.

In some examples, an inline coupling device for a reamer includes a driver coupling shaft to couple with a surgical driver; an output shaft hub to couple with a reamer driveshaft of a reamer; an electrostatic clutch assembly to engage or disengage torque from the driver to the reamer driveshaft, wherein the electrostatic clutch assembly includes: a driving plate; a driven plate; a wireless communications interface coupled with the driving plate; clutch driver circuitry coupled with the driving plate; a battery coupled with the driving plate, the wireless communications interface, and the clutch driver circuitry; and a housing to cover at least the driving plate and the driven plate.

In any preceding or subsequent example, the inline coupling device further includes a mount for an optical target array to couple optical targets with the housing or further including a reamer including the mount for an optical target array to couple with optical targets.

In any preceding or subsequent example, the inline coupling device further includes a computer system, wherein the computer system includes memory with code, wherein the code, when executed by a processor of the computer system, causes the processor to access to a translation between the optical targets and a reamer element of the reamer, determine a location of the reamer element, determine whether to engage or disengage the torque based on the location of the reamer element, and transmit a command to the wireless communications interface to engage or disengage the torque.

In any preceding or subsequent example, wherein the driving plate is coupled within the electrostatic clutch assembly proximate to driven plate via one or more fasteners.

In any preceding or subsequent example, wherein the electrostatic clutch assembly further includes a friction plate between the driving plate and the driven plate.

In any preceding or subsequent example, wherein the driving plate couples with the driver coupling shaft via a driver shaft hub and a sleeve for the driver shaft hub.

In any preceding or subsequent example, wherein the inline coupling device further includes charging circuitry to charge the battery, wherein the charging circuitry is coupled with the driving plate.

In any preceding or subsequent example, wherein the wireless communications interface includes a Bluetooth® communications interface.

In any preceding or subsequent example, wherein the battery includes a rechargeable battery.

In any preceding or subsequent example, wherein the housing for the inline coupling device is part of a handle that covers at least part of the driveshaft.

In some examples, an inline coupling device for a tool, comprising a driver coupling shaft to couple with a driver; an output shaft hub to couple with a driveshaft for the tool; a coupling device to engage, disengage, or regulate torque applied from the driver to the driveshaft; a communications interface to communicate with a computer system to receive an instruction to engage, disengage, or regulate the torque from the driver to the driveshaft; a coupling driver coupled with the coupling device to cause engagement, disengagement, or regulation of the torque applied to the driveshaft; a power source to power the communications interface and the driver; and a housing for the inline coupling device.

In any preceding or subsequent example, further comprising a mount for an optical target array to couple optical targets with the housing, wherein the housing for the inline coupling device is part of a handle that covers at least part of the driveshaft.

In any preceding or subsequent example, further comprising the computer system, wherein the computer system comprises memory with code, wherein the code, when executed by a processor of the computer system, causes the processor to access to a translation between the optical targets and an element of the tool, determine a location of the element, determine whether to engage, disengage, or throttle the torque based on the location of the element, and transmit a command to the wireless communications interface to engage, disengage, or throttle the torque.

In any preceding or subsequent example, wherein the inline coupling device comprises an electrostatic clutch assembly, a friction clutch assembly with a linear actuator, a geared interface assembly, an inline brake device assembly, an electroadhesive clutch assembly, an electrorheological fluid-based clutch, or other assembly with comparable functionality.

In some examples of use, a method of reaming a patient's femur or acetabulum is provided. The method including positioning a patient in a supine position. Next, a small incision may be made to access the patient's femur via a direct anterior approach. Thereafter, the curved outer sleeve and the flexible reamer assembly may be inserted into the incision. A surgical drill may be coupled to the proximal end of the offset reamer driveshaft via an inline coupling device. Thereafter, with the surgeon holding the handle of the outer sleeve, the patient's femur may be reamed as needed.

Examples of the present disclosure provide numerous advantages. For example, utilizing a tracking system with an offset reamer may facilitate navigation assisted surgery or robotic assisted surgery. In addition, the mounting systems for the optical and/or electromagnetic tracking systems coupled with the housing of the inline coupling device or the reamer may allow the surgeon flexibility in placement of the tracking system mounted to the reamer to accommodate various surgical situations such as the position of the patient, placement of the reamer, location of the bone for the surgical procedure, and/or the like.

Further features and advantages of at least some of the examples of the present disclosure, as well as the structure and operation of various examples of the present disclosure, are described in detail below with reference to the accompanying drawings.

BRIEF DESCRIPTION OF THE DRAWINGS

By way of example, specific examples of the disclosed device will now be described, with reference to the accompanying drawings, in which.

Figure 1:
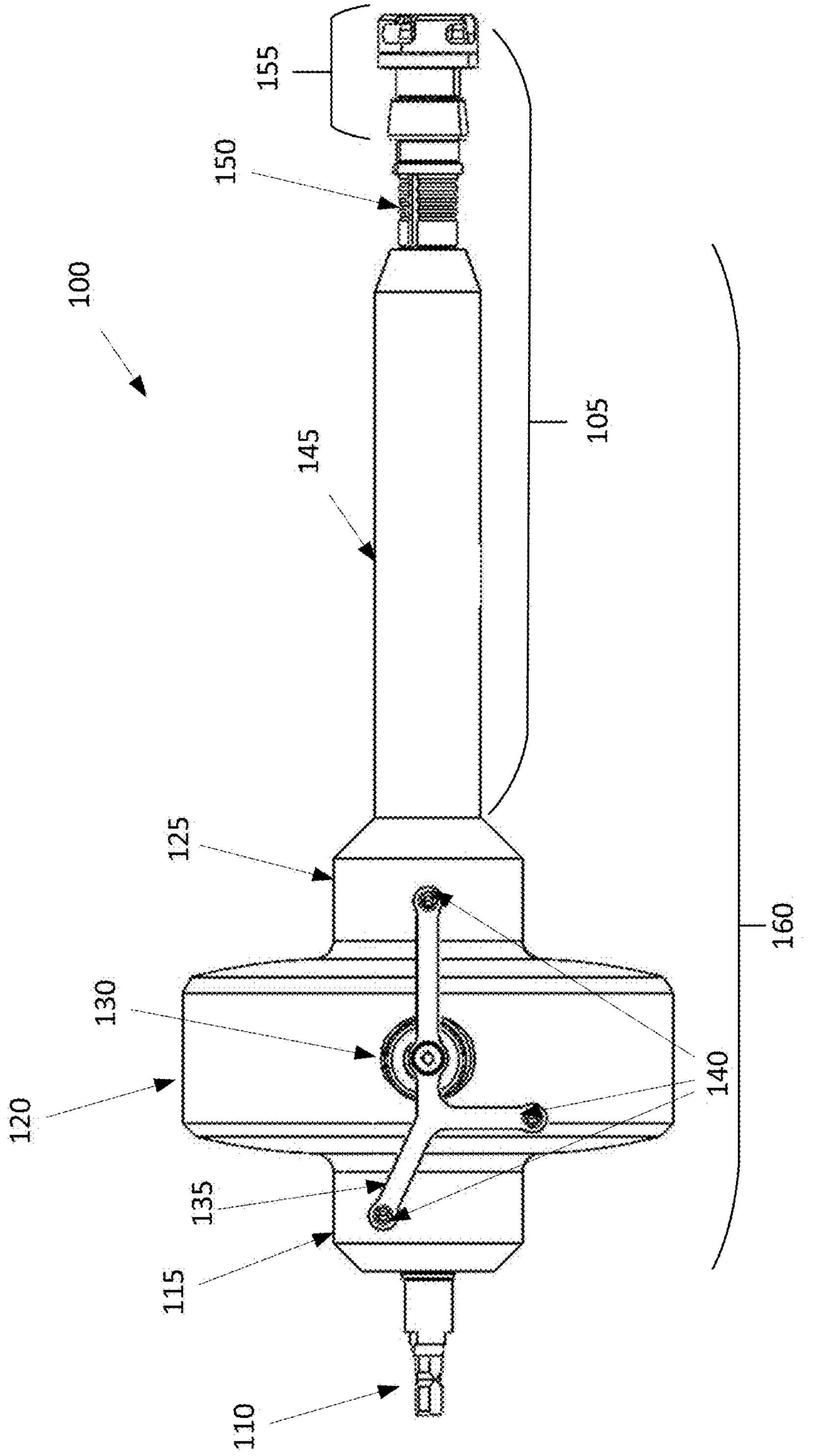
FIG. 1 illustrates a perspective view of an example of a reamer with an inline coupling device and an optical tracking array.

The drawings are not necessarily to scale. The drawings are merely representations, not intended to portray specific parameters of the disclosure. The drawings are intended to depict various examples of the disclosure, and therefore are not considered as limiting in scope. In the drawings, like numbering represents like elements.

DETAILED DESCRIPTION

Various features or the like of an offset reamer with a tracking system will now be described more fully herein with reference to the accompanying drawings, in which one or more features of the offset reamer with the tracking system will be shown and described. It should be appreciated that the various features may be used independently of, or in combination, with each other. It will be appreciated that the instrumentation set as disclosed herein may be embodied in many different forms and may selectively include one or more concepts, features, or functions described herein. As such, the offset reamer with the tracking system should not be construed as being limited to the specific examples set forth herein. Rather, these examples are provided so that this disclosure will convey certain features to those skilled in the art.

In accordance with one or more features of the present disclosure, an inline coupling device for remotely engaging and disengaging torque from a surgical for a reamer is disclosed. In use, as will be described in greater detail herein, the examples couple inline coupling device to the reamer with an optical or electromagnetic target array to engage or allow engagement of the torque to the reamer while the reamer is correctly positioned and oriented for reaming a bone in accordance with a preoperative (pre-op) plan.

A computer system may track the position and orientation of a reamer element of the reamer based on the location of the optical target array or an electromagnetic target array to allow the torque of a surgical driver to apply to a driveshaft of the reamer while the reamer element (also referred to as a reamer dome) is in positions and orientations in accordance with the preoperative plan. The computer system may have known translations stored in the memory of or in memory accessible by the computer system with respect to the optical or electromagnetic target array and may monitor the position and orientation of the optical or electromagnetic target array via one or more sensors such as an optical sensor or camera or a magnetic or electromagnetic sensor as appropriate. The computer system may, based on a determined or calculated position and orientation of the reamer element, wirelessly transmit instructions to the inline coupling device to engage or disengage the torque from the reamer to ensure that the reamer only reams the bone when in the proper positions and orientations in accordance with the preoperative plan.

The reamer dome connects to a driveshaft of a reamer such as a straight reamer or an offset reamer. In some examples, an optical tracking array mount couples with the reamer handle or reamer body or reamer sleeve in one or more positions at which a translation between the optical tracking array and the reamer element is known. In other examples, the optical tracking array mount couples with the inline coupling device in one or more positions at which a translation between the optical tracking array and the reamer element is known. The translation may refer to coordinates in three-dimensional space such as Cartesian coordinates although such a translation is not limited to any particular coordinate system. Note that while the present disclosure illustrates a limited number of different reamers, the types and lengths of the reamers are not limited to the examples illustrated.

Recent developments in navigated surgery and robotic surgery techniques have led to interest in monitoring the progression of surgery and assisting in navigation of surgical instruments during surgery including positioning and orientation of surgical tools with respect to, e.g., a bone. For instruments such as a reamer, different means are employed such as robotically positioning and orienting a sleeve for a reamer to limit movement of the reamer as an added safety measure. To implement an optical means (such as one or more cameras coupled with a computer system) for an optical tracking system, the optical means must have an unobstructed line-of-sight view of an optical tracking array on an instrument so the position of, e.g., a reamer element, is known to the computer system. The computer system may include memory with code (or instructions), wherein the code, when executed by a processor of the computer system, causes the processor to access to a translation between the optical targets on an optical tracking array and the reamer element and may determine a location of the reamer element at the distal end of the reamer based on the position of the optical targets and the translation.

Examples herein advantageously disclose solutions for attachment of an inline coupling device as an added safety measure to a reamer such that torque may be applied to the reamer element while the reamer element is at a location with respect to a bone to ream the bone in accordance with a preoperative plan. The inline coupling device may receive wired or wireless instructions from the computer system to engage or disengage torque from a surgical driver based on the location of the reamer element with respect to a bone to be reamed in accordance with a preoperative plan. In further examples, the online coupling device may also employ torque limiting features to limit torque applied the driveshaft of the reamer to a fixed or selectable torque. In such examples, the surgical driver may continuously apply torque to the inline coupling device but the torque may only be applied to the driveshaft of the reamer when the reamer element of the reamer is correctly located to ream a bone in accordance with a preoperative plan.

In accordance with one or more features of the present disclosure, with reference to FIGS. 1-5, there are shown different examples of inline coupling devices coupled with reamers as well as details of components of different online coupling devices.

FIG. 1 illustrates a perspective view of an example 100 of a reamer 105 coupled with an inline coupling device within a housing 120 and an optical tracking array 140. The inline coupling device within the housing 120 may include an exposed driveshaft 110 at a proximal end of the inline coupling device and a housing 115 for a driver shaft hub for coupling the inline coupling device with a surgical driver (not shown). In some examples, the driveshaft 110 may couple with any existing surgical driver. For instance, the surgical driver may be a standard or off-the-shelf (OTS) surgical driver.

The inline coupling device may engage, disengage, reduce, increase, throttle, regulate, and/or the like, torque applied by the surgical driver to the driveshaft 150 of the reamer 105. In some examples, the inline coupling device may adjust torque applied from the surgical driver to the driveshaft 150 of the reamer 105 by adjusting friction between clutch plates of the inline coupling device.

The inline coupling device within the housing 120 may include or couple with a housing 125 for an output shaft hub at a distal end of the online coupling device for coupling the inline coupling device with the driveshaft 150 of the reamer 105. In some examples, the housing 120, the housing 125, and a driveshaft cover 145 may comprise an integrated reamer handle 160 (a single housing) to house the inline coupling device and a driveshaft 150 of the reamer 105. Note that, in some examples, the reamer 105 may include a standard or OTS reamer and may be an inline reamer or an offset reamer.

Note that while many examples discussed herein describe a reamer coupled with the inline coupling device, examples are not so limited. Examples may comprise any tool coupled with the inline coupling device that may benefit from limiting, regulating, or throttling action of the tool based on the position of the tool with respect to a structure or patient such as a bone, a blood vessel, an organ, a nerve or nerve cluster, or the like. For instance, tools that may benefit from integration with inline coupling devices described herein may include tools for drilling, burring, abrading, and/or the like. In such examples, the inline coupling device may engage, disengage, limit, regulate, or throttle action of an element of the tool for drilling, burring, abrading, and/or the like, based on a coupling between the element of the tool and a driveshaft of the tool. Note also that the tool may be a standard or OTS tool, or may be a tool configured for integration with an inline coupling device. Similarly, the driver for a tool may be a standard or OTS driver, or may be a driver configured for integration with an inline coupling device.

In some examples, the inline coupling device includes an electrostatic clutch assembly, an electrostatic particle clutch assembly, an electroadhesive clutch assembly, a friction clutch assembly with a linear actuator, a geared interface such as a sliding mesh transmission, an inline brake device such as an electromagnetic particle brake, an electrorheological fluid-based clutch or brake, any other clutch-like mechanism, or the like. In some examples, clutch assemblies may include clutch plates including one or more driving plates coupled with the surgical driver and one or more driven plates coupled with the driveshaft of the reamer or other tool.

In some examples, the inline coupling device may include the electrostatic (or electromagnetic) clutch assembly, which may have different configurations. For instance, an electrostatic clutch assembly may include a driving plate coupled with a driver and a driven plate coupled with the reamer driveshaft. In such examples, the application of a voltage to windings on the driven plate to generate an electrostatic field that pulls the driven plate to the driving plate and friction between the plates may cause the driving plate to transmit torque to the driven plate. In some examples, a friction plate may reside between the driving plate and the driven plate to increase friction between the driving plate and the driven plate, increasing the maximum torque transmission. In some examples, since the surface area of contact between the clutch plates is directly related to the friction between the driving plate and the driven plate, multiple driving plates and multiple driven plates reside between the driving plate shaft hub and the driven plate shaft hub. In some of these examples, the diameter of the plate may be reduced with an equivalent maximum torque transmission for clutch assemblies with multiple driving and driven plates. In some examples, friction plates may reside between each of the multiple driving plates and driven plates to further increase the maximum achievable torque transmission.

In some examples, the torque transmission from the driving plate(s) to the driven plate(s) may be limited by adjusting or setting the voltage and/or current applied to the windings on the driving plate(s). For example, the voltage applied to the electrostatic clutch assembly can be modulated such that the maximum torque applied to the bone via the reamer is a pre-selected value and not just on or off. In such examples, the maximum torque may be varied with respect to patient bone quality, anatomy, surgical procedure, reaming depth, etc. In some examples, the transmitted torque may be limited by setting or pre-selecting a duty cycle for application of a voltage and current to the windings on the driving plate (and/or driving plate) to generate an electrostatic field that pulls the driven plate to the driving plate. In such examples, the duty cycle may be a pre-selected or dynamically selectable range from a 0% duty cycle to a 100% duty cycle or any sub-range thereof. The maximum torque transmitted to the bone may be a percentage of the maximum torque capability that is directly related to the selected or pre-selected duty cycle. In some examples, the duty cycle may be selected or pre-selected via the computer system, via a switch or interface within the electrostatic clutch assembly (or other inline coupling device), or on an outside surface of the housing of the electrostatic clutch assembly (or other inline coupling device. For instance, the switch or interface may include a dip switch coupled with the clutch driver circuitry (or driver circuitry of another type of inline coupling device). The dip switch may include one or more switches such as one switch to select between two different duty cycles or N switches (e.g., between 1 and 10) to select between N or more different duty cycles, where N is any positive integer. In further examples, the selectable options for the duty cycle may be presented to a user or the surgeon in the form of a duty cycle in units of time, a percentage of a duty cycle or a maximum torque, or as an actual maximum torque for each setting of the duty cycle. In some examples, the selectable settings may be presented via a graphical user interface on a display of the computer system or as markings on or proximate to the switch or interface within or on a housing of the electrostatic clutch assembly (or other inline coupling device).

In some examples, the inline coupling device may include the electrostatic (or magnetic) particle clutch assembly. The electrostatic (or magnetic) particle clutch assembly may include one or more driving plate(s) and one or more driven plate(s) and charged particles that may be suspended in an oil, a graphite powder, or the like. When the current passes through the charged particles, it generates a magnetic field that binds the particles in the form of a chain, creating a link between the clutch plates (the driving plate(s) and the driven plate(s)). The link strength can be altered with increased current and/or increased voltage. These electrically charged magnetic particles create friction within clutch plates (driving plate(s) and driven plate(s)). When the current is removed from the windings in the particle clutch assembly, the clutch plates are no longer coupled together and the driving plate(s) may rotate freely with the driven shaft minus some drag caused by the magnetic particle units located within the powder or oil cavity.

In some examples, the inline coupling device may include the electroadhesive clutch assembly. The electroadhesive clutch assembly may include one or more driving plates and one or more driven plates, wherein each of the clutch plates include an electrode coated with a high-dielectric insulator and carbon fiber attachments. In such examples, applying a voltage across the electrodes causes opposite electric charges to accumulate on the electrode surfaces of a driving plate and a driven plate. As the charge increases, an electrostatic attraction develops at the interface and the clutch plates adhere to one another. When the carbon fiber attachments of each clutch plate are pulled away from one another, the adhesion and friction at the interface of the clutch plates cause a shear force that resists relative motion. Discharging the electrodes eliminates the electrostatic attraction at the interface of the clutch plates, allowing them to release and slide freely.

In some examples, the inline coupling device may include the electrorheological (ER) fluid-based clutch assembly. The ER fluid-based clutch assembly may include a driving plate and a driven plate in an ER fluid. The ER fluid may be a suspension of extremely fine non-conducting but electrically active particles (up to 50 micrometers diameter) in an electrically insulating fluid. The apparent viscosity of the ER fluid changes reversibly by an order of up to 100,000 in response to an electric field applied between the driving plate and the driven plate. For example, a typical ER fluid can go from the consistency of a liquid to that of a gel, and back, with response times on the order of milliseconds.

The change is not a simple change in viscosity, hence these fluids are now known as ER fluids, rather than by the older term Electro Viscous fluids. The effect is better described as an electric field dependent shear yield stress. When activated an ER fluid behaves as a Bingham plastic (a type of viscoelastic material), with a yield point which is determined by the electric field strength. After the yield point is reached, the fluid shears as a fluid, i.e., the incremental shear stress is proportional to the rate of shear. Hence the resistance to motion of the fluid can be controlled by coupling driver circuitry by adjusting the applied electric field. When the electric field is applied, the driving plate and the driven plate of an ER clutch assembly are locked together. When the electric field is removed from the ER, the clutch plates are disengaged.

In some examples, the inline coupling device may include the sliding mesh clutch assembly. The sliding mesh clutch assembly may include a transmission system including multiple sets of gears and shafts arranged to enable gear shifting or meshing of different gear ratios through the movement of gears along the splined shaft by coupling driver circuitry. By sliding gears in one direction or an opposite direction along the splined shaft, the desired gear ratio can be engaged, allowing the transmission of torque from the surgical driver to the driveshaft of the reamer.

In some examples, the inline coupling device may include the friction clutch assembly with a linear actuator. The friction clutch assembly with a linear actuator may include one or more driving plates and one or more driven plates wherein a linear actuator (such as a spring, a solenoid, or the like) drives the driven plate into the driving plate to engage the friction clutch assembly. In some examples, a friction plate may reside between the driving plate and the driven plate to increase friction between the driving plate and the driven plate, increasing the maximum torque transmission. In some examples, since the surface area of contact between the clutch plates determines the friction between the driving plate and the driven plate, multiple driving plates and multiple driven plates reside between the driving plate shaft hub and the driven plate shaft hub to reduce the diameter of the clutch plates without impacting the maximum torque transmission capability of the assembly. In some examples, friction plates may reside between each of the multiple driving plates and multiple driven plates to further increase the maximum torque transmission capability of the assembly. In some examples, the torque transmission from the driving plate(s) to the driven plate(s) may be limited by adjusting or setting the voltage and/or current applied to the winding of a solenoid. In such examples, a wired or wireless communications interface, charger circuitry to charge a power source, the power source such as a battery, and coupling driver circuitry may couple with the driving plate, driven plate, an adapter plate attached to the driving plate and/or the driven plate, or otherwise be mounted near the linear actuator to activate the linear actuator in response to an instruction from the wired or wireless communications interface via the coupling driver circuitry to engage the clutch plates.

In some examples, an adapter plate is added to one or more driving plate(s) and/or driven plate(s) to mount components such as a wired and/or wireless communications interface, charging circuitry for a power source such as a rechargeable battery (for applications in which the battery is rechargeable), the power source such as a battery (rechargeable or single use), and coupling driver circuitry such as clutch driver circuitry to apply power from the battery to winding(s), electrodes, plates, ER fluid, or the like, in or about one or more clutch plates (or electroadhesive plates) based on engagement and disengagement instructions received via the wired or wireless communications interface at a voltage of the power source or at a voltage and/or current designated to limit the torque transmitted to the driving plate(s) (or electroadhesive plates).

In other examples, rather than including a wireless communications interface, a wired interface may provide instructions to the coupling driver circuitry to energize and deenergize winding(s), electrodes, plates, ER fluid, or the like.

In some examples, the inline coupling device may include the inline brake device such as an electromagnetic particle brake. The electromagnetic particle brake may operate similarly to the electromagnetic particle clutch except that permanent magnets may establish the electromagnetic field to cause the particles in the particle solution to couple the driving plate(s) and the driven plate(s) to transmit torque from the surgical driver to the driveshaft of the reamer. When a instruction is received by a wired or wireless communication interface, a coupling driver circuit may apply a voltage from a power source coupled with the driving plate(s) and/or driven plate(s) to apply an electromagnetic field between the driving plates and the driven plates that is opposite the magnetic field established by the permanent magnets (which may be mounted on the driving plate(s) and the driven plate(s)) to reduce or remove (negate) the magnetic field established by the permanent magnets.

In some examples, the inline coupling device may include the inline brake device such as a spring-type brake. The spring-type brake may operate similarly to the electromagnetic clutch assembly except that one or more springs may push the driven plate against an outer plate or a friction plate between the driven plate and the outer plate to brake the driven plate when power is not applied to the windings of the driving plate. With power applied to the windings of the driving plate, the electromagnetic field may exert force to counteract the spring force and to pull the driven plate towards the driving plate. When an instruction is received by a wired or wireless communication interface to engage the clutch plates, coupling driver circuitry may apply a voltage and current from a power source coupled with the driving plate and/or driven plate to the windings of the driving plate and/or driven plate.

In some examples, the wireless communications interface may implement wireless communications in accordance with one or more wireless standards and/or specifications. For instance, the wireless communications interface may facilitate communications in accordance with one or more versions of Institute of Electrical and Electronics Engineers (IEEE) 802.11 standards for wireless communications such as IEEE P802.11be™/D1.0, May 2021; IEEE 802.11-2020, December 2020; IEEE P802.11ax™/D8.0, IEEE P802.11ay™/D7.0, IEEE P802.11az™/D3.0, IEEE P802.11ba™/D8.0, IEEE P802.11bb™/D0.4, IEEE P802.11bc™/D1.02, and IEEE P802.11bd™/D1.1. The wireless communications interface may facilitate communications in accordance with one or more versions of Bluetooth® specifications such as Bluetooth Core specifications 5.0 through 5.4, as well as older Bluetooth® specifications such as 3.0, 4.0, which includes Bluetooth® low energy (BLE) specifications.

In the illustrated example 100, the inline coupling housing includes a mount 130 for a target array mount 135. The target array mount 135 may couple with an array of optical targets 140. In some examples, the target array mount 135 may couple with an array of electromagnetic targets.

The reamer 105 includes a driveshaft cover 145 (or reamer handle) to cover a portion of the driveshaft 150 of the reamer 105 and a reamer element coupling 155 at a distal end of the reamer 105. The reamer element coupling may couple with a reamer element such as a reamer dome for reaming a bone. The housing 145 for the driveshaft 150 may include a tubular cover having a rotating element that may be concentric with or otherwise within the tubular cover. In some examples, the driveshaft cover 145 is integrated with the inline coupling device or a cover for the inline coupling device.

Figure 2:
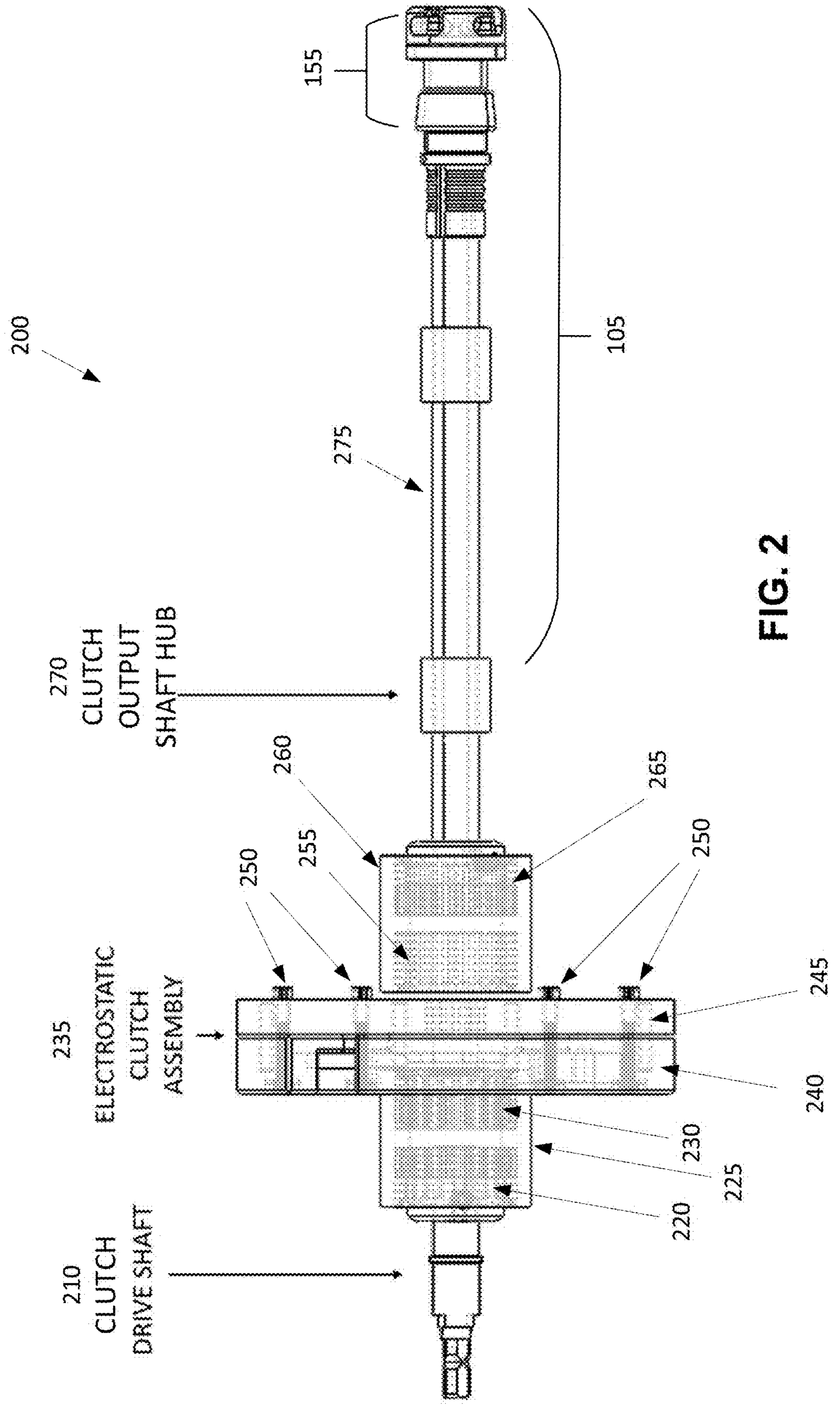
FIG. 2 illustrates a perspective view of another example of a reamer with an inline coupling device that is an electrostatic clutch assembly.

FIG. 2 illustrates a perspective view of another example of the reamer 105 with an inline coupling device that is an electrostatic clutch assembly 235. The electrostatic clutch assembly 235 includes a clutch drive shaft 210, at a proximal end of the electrostatic clutch assembly 235, coupled with a driver shaft hub 220. The driver shaft hub 220 may couple with a driver shaft hub sleeve 225 wherein both the driver shaft hub 220 and the driver shaft hub sleeve 225 include gears or teeth that interconnect transmit torque from the clutch driver shaft 210 to the driver shaft hub sleeve 225. The driver shaft hub sleeve 225 also includes gears or teeth to transmit the torque from the driver shaft hub sleeve 225 to a driving plate shaft hub 230. The driving plate shaft hub 230 couples with a driving plate 240 (also referred to as a flywheel or an electrostatic driving plate) to receive the torque from the driving plate shaft hub 230.

The electrostatic clutch assembly 235 includes a first housing including the driving plate 240, a second housing including a driven plate 245, and fasteners 250 to couple the first housing to the second housing to maintain the driving plate 240 proximate to the driven plate 245. In some examples, the driving plate 240 and the driven plate 245 may be made of metal or a metal alloy and may be mounted on separate shafts. When no voltage is applied to the driving plate 240, the driving plate 240 and the driven plate 245 may be separated by a gap such as an air gap, preventing torque transmission from the driving plate 240 to the driven plate 245. To engage the clutch plates, a high voltage is applied to the driving plate 240, which generates an electrostatic field. The electrostatic field induces an opposite charge on the driven plate 245, creating an attractive force that pulls the clutch plates together. As the clutch plates come into contact, torque is transmitted from the driveshaft 210 to the driven shaft hub 255.

The electrostatic force is proportional to the square of the applied voltage and inversely proportional to the square of the air gap distance. By controlling the voltage via clutch driver circuitry (not shown), the torque transmitted from the driving plate 240 to the driven plate 245 can be adjusted or limited, allowing for precise control of the electrostatic clutch assembly's 235 engagement and disengagement. In some examples, the clutch driver circuitry may apply a fixed voltage and/or current to the driving plate 240 to fix a limit on the torque transmitted from the driving plate 240 to the driven plate 245. In some examples, a computer system may select a limit for the torque transmission from the driving plate 240 to the driven plate 245 by communicating an indication of the limit for the torque to the clutch driver circuitry (not shown). In further examples, the limit for the torque may be adjustable at the electrostatic clutch assembly 235, either via a switch or other interface within the electrostatic clutch assembly 235 or via a switch or other interface on the outside of the housing of the electrostatic clutch assembly 235 such that a surgeon may adjust the limit for the torque transmission as needed.

The driven plate 245 may couple with a driven plate shaft hub 255. The driven plate shaft hub 255 may couple with a driven plate shaft hub sleeve 260 wherein both the driven plate shaft hub 255 and the driven plate shaft hub sleeve 260 include gears or teeth that interconnect to transmit torque from the driven plate 245 to driven plate shaft hub sleeve 260. The driven plate shaft hub sleeve 260 also includes gears or teeth to transmit the torque from the driven plate shaft hub sleeve 260 to a driven plate shaft hub 265. The driven plate shaft hub 265 transmits the torque received at the driven plate 245 to a reamer driveshaft 275 of the reamer 105 via a clutch output shaft hub 275 and the clutch output shaft hub 275 transmits the torque to the reamer element coupling 155 via the reamer driveshaft 150.

Figure 3:
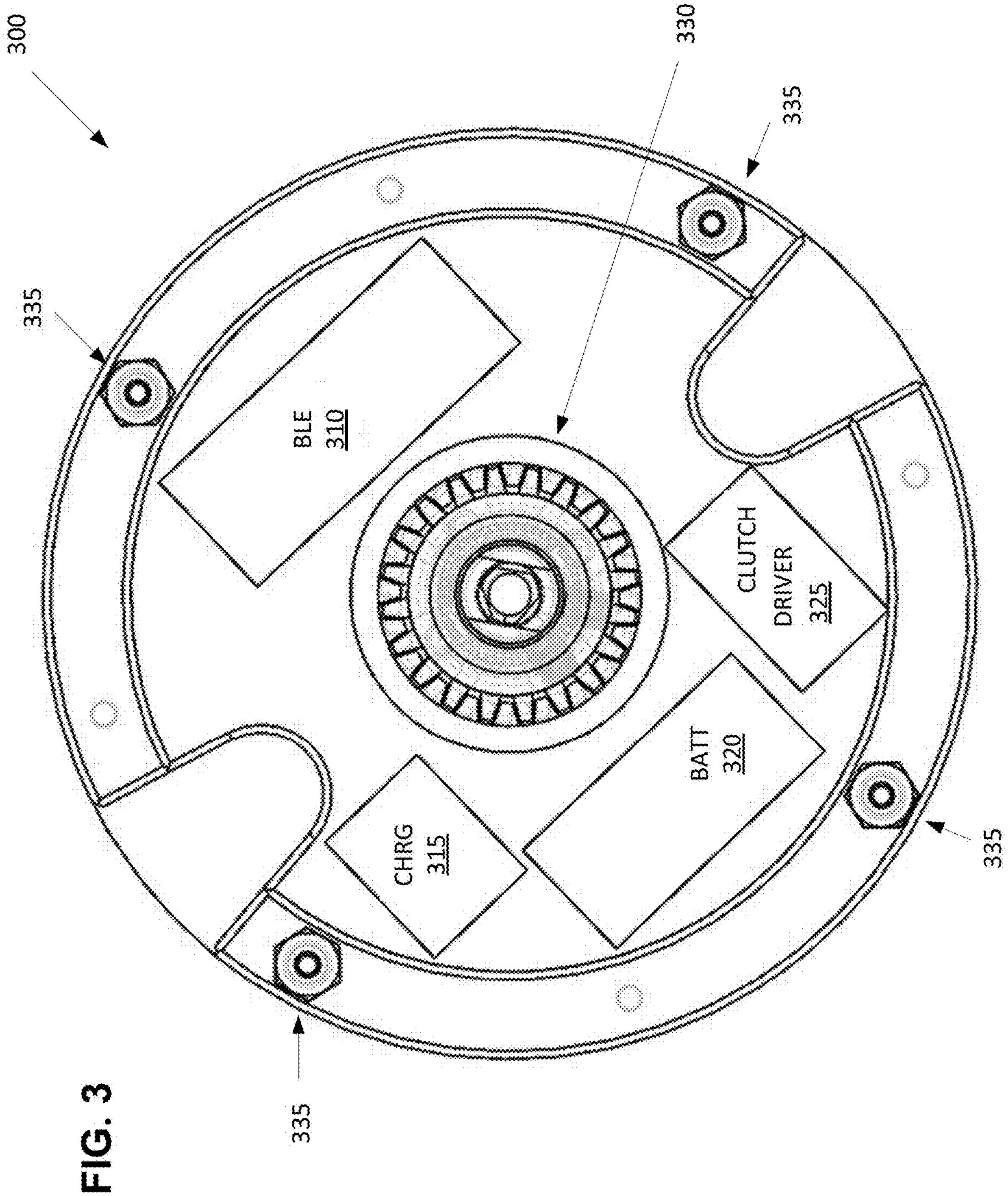
FIG. 3 illustrate a perspective view of an example of an electrostatic plate for an electrostatic clutch assembly such as the electrostatic clutch assembly in FIG. 2.

FIG. 3 illustrates a perspective view of an example of an electrostatic driving plate 300 for, e.g., an electrostatic clutch assembly such as the electrostatic clutch assembly 235 in FIG. 2. In various examples, the electrostatic driving plate 300 may be a driving plate, a driven plate, or an adapter plate for an electrostatic clutch assembly, a friction clutch assembly with a linear actuator, a geared interface assembly, an inline brake device assembly, an electroadhesive clutch assembly, an electrorheological fluid-based clutch assembly, or other assembly with comparable functionality. In other examples, the components attached to the electrostatic driving plate 300 may attach at other locations inside the housing of the assembly or on the outside of the assembly.

The electrostatic driving plate 300 includes a driver shaft hub 330, a Bluetooth® Low Energy wireless communications interface 310, charging circuitry 315, a battery 320, and clutch driver circuitry 325 coupled with a first surface of the electrostatic driving plate 300. The electrostatic driving plate 300 may include windings (not shown) to generate an electrostatic field. In this example, the first surface of the electrostatic driving plate 300 is opposite a second surface of the electrostatic driving plate 300. The second surface to contact a surface of a friction plate between the electrostatic driving plate 300 and the driven plate (also referred to as a pressure plate) when the driven plate (not shown) is pulled toward the electrostatic driving plate 300 via an electrostatic field generated by the windings when the voltage is applied to the windings to engage the clutch plates. In other examples, the second surface of the electrostatic driving plate 300 may contact the driven plate directly (no friction plate in between) when a voltage is applied to the windings of the electrostatic driving plate 300.

The friction plate may modify a coefficient of friction between the electrostatic driving plate 300 and the driven plate. In many examples, the coefficient of friction is increased by the addition of a friction plate between the electrostatic driving plate 300 and the driven plate, increasing the maximum torque transmission capability of the electrostatic clutch assembly.

In response to a Bluetooth® communication from a computer system to the BLE 310 such as a data packet including a field defined for engagement or disengagement, the BLE 310 may decode the data packet to determine a value in the field and pass the value to the clutch driver circuitry 325. In some examples, a processor of the BLE 310 may determine the value of the field, interpret the value, and provide an instruction to the clutch driver circuitry 325 based on the value. For instance, the value may include a logical zero bit to indicate disengagement, a logical one bit to indicate engagement, or vice versa. In response to the value of the bit, the BLE 310 may apply a voltage to an input of the clutch driver circuitry 325. If the value indicates engagement, the BLE 310 may apply a voltage of 5 volts, 2.5 volts, 1 volt, any voltage between 1 and 5 volts, or the like to the input of the clutch driver circuitry. If the value indicates disengagement, the BLE 310 may apply a voltage of negative 5 volts, negative 2.5 volts, negative 1 volt, zero volts, circuit ground, any voltage between −1 and −5 volts, or the like to the input of the clutch driver circuitry. In other examples, the voltages applied by the BLE 310 to the input of the clutch driver circuitry may be reversed for engagement and disengagement.

Note that the BLE 310 may include a wireless communications interface for any one or more different wireless standards or specifications. The data packet and the filed may include the same data as discussed above and the wireless communications interface may apply the same or similar voltages to the input of the clutch driver circuitry 312 in response. Not that the actual voltages used may be based on the configuration of the wireless communications circuitry, i.e., voltages available to the communications circuitry from the power source such as the battery 320, operational voltages of the wireless communications interface, and operational voltages of the clutch driver circuitry (or coupling driver circuitry for other types of assemblies).

In response to the input from the BLE 310 indicating engagement, the clutch driver circuitry 325 may apply a voltage to the windings of the electrostatic driving plate 300 such as connecting the windings to the battery 320. In response to the input from the BLE 310 indicating disengagement, the clutch driver circuitry 325 may remove a voltage from the windings of the electrostatic driving plate 300 or disconnect the windings from a voltage such as disconnecting the windings from the battery 320.

When a voltage is applied to the windings (not shown) from the battery 320 via the clutch driver circuitry 325, the current through the windings may determine the normal force applied from the driven plate to the electrostatic driving plate 300 and the torque transmission from the electrostatic driving plate 300 to the driven plate may be based on the coefficient of friction between the electrostatic driving plate 300 and the driven plate and the normal force applied by the driven plate to the electrostatic driving plate 300.

In some examples, the electrostatic driving plate 300 may include fasteners 335 to couple an adapter plate to the electrostatic driving plate 300. In some examples, the electrostatic driving plate 300 is the adapter plate that includes the driving plate shaft hub 330 and couples with the driving plate via the fasteners 335.

In further examples, the charger circuitry 315 may include or be coupled with energy harvesting circuitry to capture energy from rotation of the electrostatic driving plate 300. The energy harvesting circuitry may store energy captured in the battery 320 to recharge the battery while the surgical driver (not shown) is driving the electrostatic driving plate 300.

Figure 4:
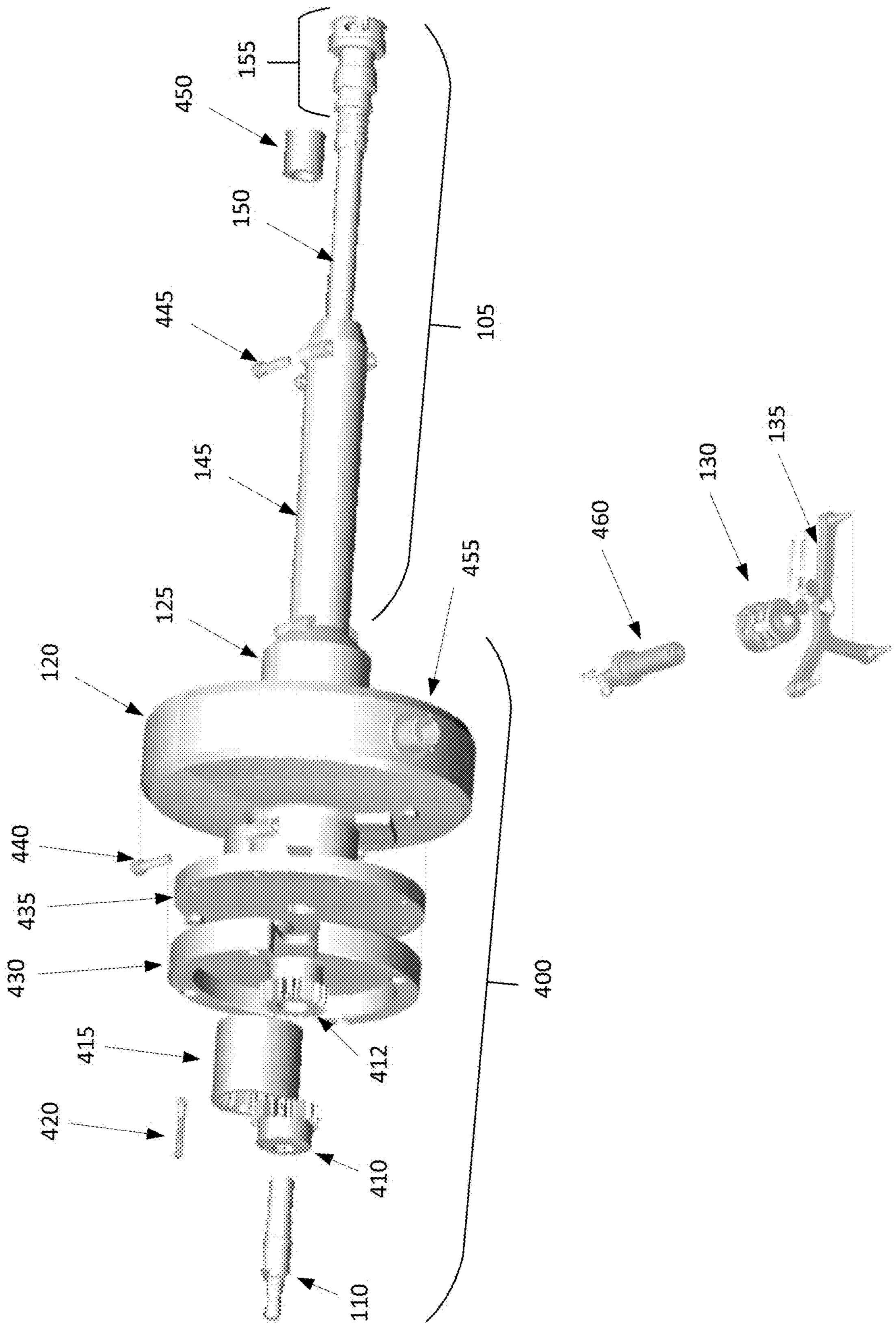
FIG. 4 illustrates a perspective view of an example of a reamer with an inline coupling device that is an assembly such as the electrostatic clutch assembly in FIG. 2.

FIG. 4 illustrates an exploded perspective view of an example of a reamer 105 with an inline coupling device 400 that is an assembly such as the electrostatic clutch assembly in FIG. 2. The inline coupling device 400 may include a driver shaft coupling 110, a driver shaft hub 410, a driver shaft hub sleeve 415, a driving plate 430 with a driving plate shaft hub 412, a fastener 420 to couple an adapter plate with a driving plate, and a driven plate 435. The inline coupling device 400 may also include fasteners 440 to couple the housing 120 together at the housing for the driving plate shaft sleeve and the housing 125 for the output shaft hub. In some examples, the housing 120 may also include a mount 130 for an optical target array via a target array shaft 460, a target array mount coupling 455 and a target array mount 135.

The reamer 105 may couple with inline coupling device 400 at the housing 125 for an output shaft hub at the proximal end of the reamer 105. The reamer 105 may include a reamer housing 145 coupled with the reamer 105 via fasteners 445, a reamer driveshaft 150 coupled with the output shaft hub, and a bearing sleeve 450 about the reamer shaft 150 within the reamer housing 145 to maintain a spacing between the reamer driveshaft 150 and the reamer housing 145. The reamer 105 may also include a reamer element coupling 155 at the distal end of the reamer 105.

Note that the reamers illustrated herein are examples. Examples may use straight reamers and offset reamers of any length and with various different mounting positions for the optical tracking array so long as the computer system can determine the translation between the optical tracking array and the reamer element or a point on the reamer element.

In addition, and/or alternatively, in some examples, the reamer may include one or more position sensors such as, for example, sensor arrays, which may be coupled to, for example, the outer sleeve, to track the location of the instrument. Tracking the instrumentation during the femoral reaming workflow may enable live measurement of femoral instrument alignment with respect to the native femoral axis. Tracking this metric may reduce the risk encountered with femoral reaming of puncturing the face of the femur. Thus arranged, the reamer may be used in a surgical navigation system. As such, during use, the location, direction, and depth may be tracked to prevent, or at least minimize, over-drilling the patient's bone.

In use, the reamer sleeve can be manufactured from any suitable rigid material such as, for example, any surgical metal such as, for example, titanium, titanium alloys, stainless steel, cobalt-chromium alloys, tantalum, or the like.

Figure 5:
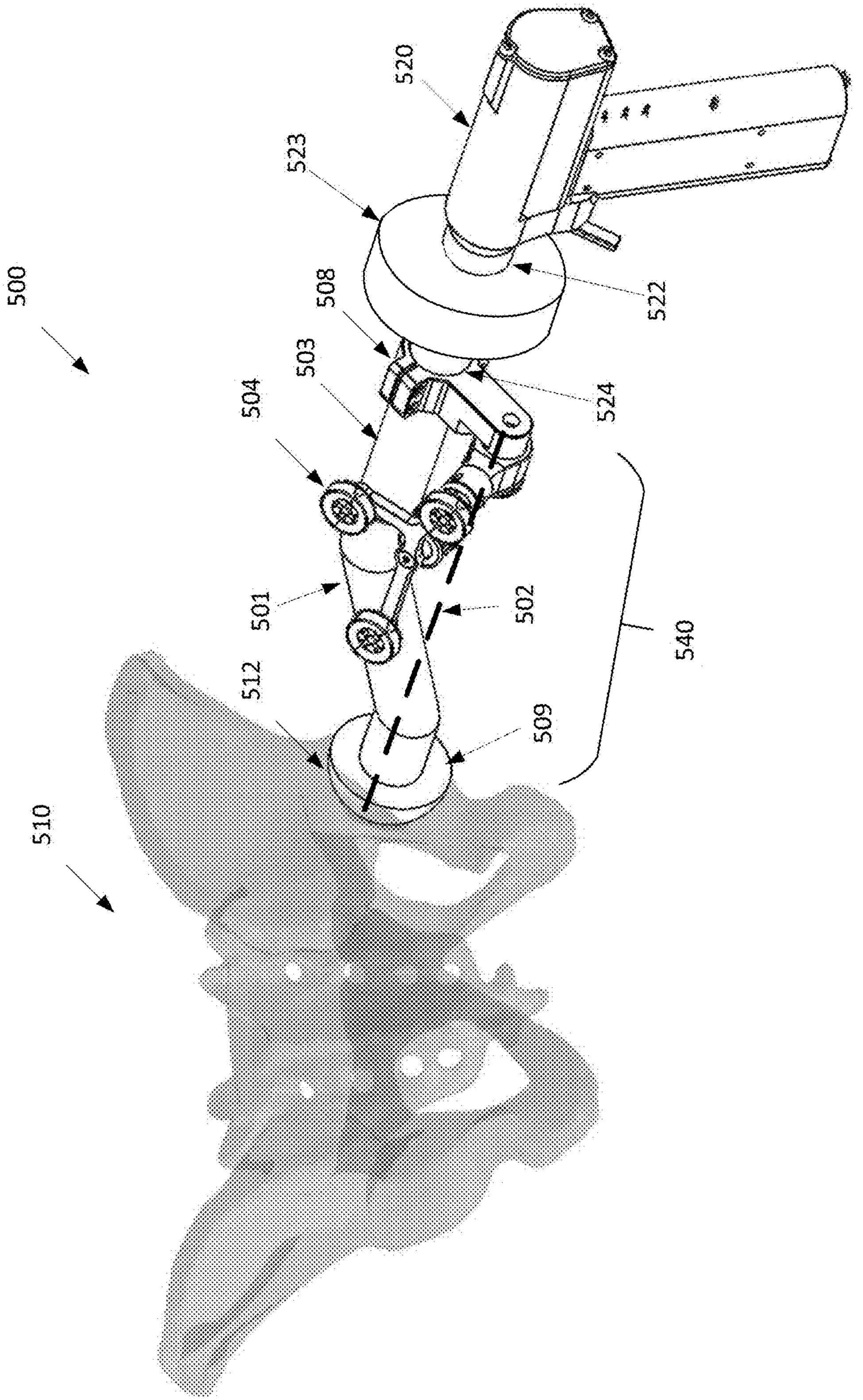
FIG. 5 illustrates a perspective view of an example of an offset reamer with an inline coupling device and an optical tracking array with the reamer element in the acetabulum for preparation of the acetabular cup for total hip arthroplasty.

FIG. 5 illustrates a perspective view of another example 500 of the offset reamer 540 having an inline coupling device 523 and an optical or electromagnetic tracking array 504 with the reamer element 509 in the acetabulum 512 for preparation of an acetabular cup on a pelvis bone 510 for total hip arthroplasty (THA). During the preparation of the acetabular cup on a pelvis bone 510, the surgeon removes portions of the acetabulum 512 to form the acetabular cup. Formation of the acetabular cup in a proper position is critical to successful total hip replacement. Improper placement of the acetabular cup can lead to increased rates of dislocation, wear, and ion toxicity. The optimal cup position for individual patients depends on differences in functional pelvic position, surgical approach, and femoral anteversion. Note that the offset reamer 540 is similar to the straight reamer 105 shown in FIGS. 1-4 except for the offset portion 501 of the reamer driveshaft that creates an offset axis for reaming 502 but other examples may use a straight reamer similar to the straight reamer 105 or a different offset reamer for preparation of an acetabular cup on a pelvis bone 510 for THA.

A surgeon may hold a surgical driver 520 coupled with the offset reamer 540 in a position and orientation to place a reamer element 509 on the acetabulum 512 for preparation of the acetabular cup on a pelvis bone 510. The surgical driver 520 includes a driver coupling 522 that couples with a driveshaft 503 of the offset reamer 540 via the inline coupling device 523 and an output shaft hub 524 to drive the reamer element 509.

The inline coupling device 523 may include an electrostatic clutch assembly 220 as shown in FIG. 2 or another inline coupling device such as a friction clutch assembly with a linear actuator, a geared interface assembly, an inline brake device assembly, an electroadhesive clutch assembly, an electrorheological fluid-based clutch, or other assembly with comparable functionality, and/or the like. In some examples, the inline coupling device may include a torque limiting feature such that the torque is limited to a fixed or selectable torque setting via a manual setting at the inline coupling device 523 and/or at a computer system communicatively coupled with the inline coupling device 523.

A mount 508 for an optical target array 504 couples with the driveshaft 503 of the offset reamer 500 to position the optical target array 504 in a position of rotation about an axis of reaming 502 that does not interfere with the surgeon and is visible to one or more cameras of an optical targeting system.

The driveshaft 503 of the offset reamer 500 includes the offset portion 501 that offsets the axis of reaming from the axis of the surgical driver 520 to the axis of reaming 502. The reamer element 509 couples with a coupling at the distal end of the offset reamer 540 for reaming the acetabulum 512.

In accordance with one or more features of the present disclosure, the offset reamer may be used to prepare a patient's acetabular in connection with a Total Hip Arthroplasty, however it should be appreciated that the present disclosure is not so limited and can be used with other implants and/or other surgical procedures such as, for example, insertion of an intramedullary nail. In addition, the present disclosure is not limited to any particular surgical approach and may be used in connection with an anterior approach, a lateral approach, a posterior approach, or any combination thereof. Thus, the present disclosure should not be limited to any particular device and/or procedure unless specifically claimed.

While the present disclosure refers to certain examples, numerous modifications, alterations, and changes to the described examples are possible without departing from the sphere and scope of the present disclosure, as defined in the appended claim(s). Accordingly, it is intended that the present disclosure not be limited to the described examples, but that it has the full scope defined by the language of the following claims, and equivalents thereof. The discussion of any example is meant only to be explanatory and is not intended to suggest that the scope of the disclosure, including the claims, is limited to these examples. In other words, while illustrative examples of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more examples or configurations for the purpose of streamlining the disclosure. However, it should be understood that various features of the certain examples or configurations of the disclosure may be combined in alternate examples, or configurations. Any example or feature of any section, portion, or any other component shown or particularly described in relation to various examples of similar sections, portions, or components herein may be interchangeably applied to any other similar example or feature shown or described herein. Additionally, components with the same name may be the same or different, and one of ordinary skill in the art would understand each component could be modified in a similar fashion or substituted to perform the same function.

Moreover, the following claims are hereby incorporated into this Detailed Description by this reference, with each claim standing on its own as a separate example of the present disclosure.

As used herein, an element or step recited in the singular and proceeded with the word "a" or "an" should be understood as not excluding plural elements or steps, unless such exclusion is explicitly recited. Furthermore, references to "one example" of the present disclosure are not intended to be interpreted as excluding the existence of additional examples that also incorporate the recited features.

The phrases "at least one," "one or more," and "and/or" as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

The invention claimed is:

1. An orthopedic instrumentation system comprising:

a computer system comprising memory with code; and an inline coupling device for a reamer comprising:

a driver coupling shaft to couple with a driver;

an output shaft hub to couple with a reamer driveshaft;

a coupling device to engage or disengage torque from the driver to the reamer driveshaft;

a communications interface to communicate with the computer system to receive an instruction to engage or disengage the torque from the driver to the reamer driveshaft;

a coupling driver coupled with the coupling device to cause engagement or disengagement of the torque;

a power source to power the communications interface and the driver; and a housing for the inline coupling device; and wherein the code, when executed by a processor of the computer system, causes the processor to access a translation between the optical targets and a reamer element of a reamer, determine a location of the reamer element, determine whether to engage or disengage the torque based on the location of the reamer element, and transmit a command to a wireless communications interface to engage or disengage the torque.

2. The orthopedic instrumentation system of claim 1, wherein the inline coupling device further comprises a mount for an optical target array to couple optical targets with the housing.

3. The orthopedic instrumentation system of claim 1, wherein the inline coupling device comprises an electrostatic clutch assembly, a friction clutch assembly with a linear actuator, a geared interface assembly, an inline brake device assembly, an electroadhesive clutch assembly, an electrorheological fluid-based clutch, or other assembly with comparable functionality.

4. The orthopedic instrumentation system of claim 1, wherein coupling device comprises an electrostatic clutch assembly, the electrostatic clutch assembly comprising an electrostatic driving plate, wherein the coupling driver, the power source, and the wireless communications interface are coupled with a surface of the electrostatic driving plate directly or via an adapter plate.

5. The orthopedic instrumentation system of claim 4, wherein the electrostatic driving plate is coupled within the electrostatic clutch assembly proximate to a driven plate via one or more fasteners.

6. The orthopedic instrumentation system of claim 5, wherein the electrostatic driving plate couples with the driver coupling shaft via a shaft hub and a sleeve for the shaft hub.

7. The orthopedic instrumentation system of claim 1, wherein the housing for the inline coupling device is part of a reamer handle that covers at least part of the reamer driveshaft.

8. An inline coupling device to couple with a reamer, comprising:

a driver coupling shaft to couple with a driver;

an output shaft hub to couple with a reamer driveshaft of the reamer;

an electrostatic clutch assembly to engage or disengage torque from the driver to the reamer driveshaft, wherein the electrostatic clutch assembly comprises:

a driving plate;

a driven plate;

a wireless communications interface coupled with the driving plate;

clutch driver circuitry coupled with the driving plate;

a battery coupled with the driving plate, the wireless communications interface, and the clutch driver circuitry; and a housing to cover at least the driving plate and the driven plate; and wherein the driving plate is coupled within the electrostatic clutch assembly proximate to the driven plate via one or more fasteners and the electrostatic clutch assembly further comprises a friction plate between the driving plate and the driven plate.

9. The inline coupling device of claim 8, further comprising a mount for an optical target array to couple optical targets with the housing or further comprising the reamer with the mount for the optical target array to couple with optical targets.

10. The inline coupling device of claim 9, further comprising a computer system, wherein the computer system comprises memory with code, wherein the code, when executed by a processor of the computer system, causes the processor to access a translation between the optical targets and a reamer element of the reamer, determine a location of the reamer element, determine whether to engage or disengage the torque based on the location of the reamer element, and transmit a command to the wireless communications interface to engage or disengage the torque.

11. The inline coupling device of claim 8, wherein the driving plate couples with the driver coupling shaft via a driver shaft hub and a sleeve for the driver shaft hub.

12. The inline coupling device of claim 11, further comprising charging circuitry to charge the battery, wherein the charging circuitry is coupled with the driving plate.

13. An inline coupling device to couple with a reamer, comprising:

a driver coupling shaft to couple with a driver;

an output shaft hub to couple with a reamer driveshaft of the reamer;

an electrostatic clutch assembly to engage or disengage torque from the driver to the reamer driveshaft, wherein the electrostatic clutch assembly comprises:

a driving plate;

a driven plate;

a wireless communications interface coupled with the driving plate;

clutch driver circuitry coupled with the driving plate;

a battery coupled with the driving plate, the wireless communications interface, and the clutch driver circuitry; and a housing to cover at least the driving plate and the driven plate;

wherein the wireless communications interface comprises a Bluetooth® communications interface.

14. An inline coupling device for a tool, comprising:

a driver coupling shaft to couple with a driver;

an output shaft hub to couple with a driveshaft for the tool;

a coupling device to engage, disengage, or regulate torque applied from the driver to the driveshaft;

a communications interface to communicate with a computer system to receive an instruction to engage, disengage, or regulate the torque from the driver to the driveshaft, the communications interface comprising a Bluetooth® communications interface;

a coupling driver coupled with the coupling device to cause engagement, disengagement, or regulation of the torque applied to the driveshaft;

a power source to power the communications interface and the driver; and a housing for the inline coupling device.

15. The inline coupling device of claim 14, further comprising a mount for an optical target array to couple optical targets with the housing, wherein the housing for the inline coupling device is part of a handle that covers at least part of the driveshaft.

16. The inline coupling device of claim 15, further comprising the computer system, wherein the computer system comprises memory with code, wherein the code, when executed by a processor of the computer system, causes the processor to access a translation between the optical targets and an element of the tool, determine a location of the element, determine whether to engage, disengage, or throttle the torque based on the location of the element, and transmit a command to the wireless communications interface to engage, disengage, or throttle the torque.

17. The inline coupling device of claim 14, wherein the inline coupling device comprises an electrostatic clutch assembly, a friction clutch assembly with a linear actuator, a geared interface assembly, an inline brake device assembly, an electroadhesive clutch assembly, an electrorheological fluid-based clutch, or other assembly with comparable functionality.

* * * * *